United States Patent
Saens-Arrollo

[11] Patent Number: 5,810,761
[45] Date of Patent: Sep. 22, 1998

[54] INTRAVENTRICULAR PRESSURE CONTROL DEVICE

[75] Inventor: Mario Saens-Arrollo, Colonia, Florida, Mexico

[73] Assignee: Biomedica Mexicana, S.A. DE C.V., D.F., Mexico

[21] Appl. No.: 805,828

[22] Filed: Feb. 26, 1997

[51] Int. Cl.$^6$ ................................... A61N 5/00
[52] U.S. Cl. ............................................. 604/9
[58] Field of Search .................. 604/8, 9, 10, 247, 604/249

[56] References Cited

U.S. PATENT DOCUMENTS

| | | | |
|---|---|---|---|
| 3,583,387 | 6/1971 | Garner | 604/9 |
| 4,681,559 | 7/1987 | Hooven | 604/9 |
| 4,705,499 | 11/1987 | Hooven | 604/9 |
| 4,787,887 | 11/1988 | Saenz Arroyo | 604/9 |
| 4,832,054 | 5/1989 | Bark | 604/9 |

Primary Examiner—David Isabella
Attorney, Agent, or Firm—Ladas & Parry

[57] ABSTRACT

The cephalorachidian liquid drain pressure control device comprising a body that can be cylindrical or any other geometrical shape, made from a rigid, biocompatible and stable plastic or other material with similar characteristics. The lower part of the body has one or several perforations and the upper part is internally threaded. It further comprises a threaded cap made from a rigid, biocompatible and stable plastic or other material with similar characteristics and having at the center thereof a perforation in which is mounted the bellows shaped elastic element controlling the drain pressure. This bellows shaped elastic element has one or more ripples or any other form allowing it to act as a spring and being provided in one of its ends with a disk shape forming part of the flow block mechanism (check). However, this flat and circular shape is not necessarily integrated with the elastic element acting as a spring.

10 Claims, 4 Drawing Sheets

INTRAVENTRICULAR PRESSURE CONTROL DEVICE

FIELD OF THE INVENTION

The invention refers to a device designed to integrate a pressure range control valve, which drains the cephalorachidian liquid during hydrocophalus treatment. It has the advantage of relieving the cephalorachidian liquid towards the peritoneum or to the right auricle (atrium dextrum) when the intraventricular pressure exceeds the desirable limits; likewise it blocks the drain hole of said liquid allowing its pressure to be kept at the required physiological levels. Other bypass systems use different control mechanisms being less accurate and with broader pressure variation ranges.

BACKGROUND OF THE INVENTION

There is a range of cephalorachidian liquid production and absorption thereof being in perfect balance in healthy people. When production of cephalorachidian liquid exceeds absorption thereof, it accumulates and constitutes the condition called hydrocephalus which is harmful to the brain's integrity.

Hydrocephalus treatment is achieved by a surgical procedure comprising the implant of a valve linked to a double drain system; one going from the brain's ventricles to the valve and the other from the valve to any area of the organism in which the cephalorachidian liquid excess is bypassed. In humans the right auricle or the peritoneal cavity is used. This treatment has been used for several decades with different bypass system models controlling in one way or another the cephalorachidian liquid exit pressure. Among this variety of designs, some are efficient and others are not efficient to achieve this goal.

All the cephalorachidian liquid systems comprise mechanical equipment comprising a pressure control valve and two oatheters,

SUMMARY OF THE INVENTION

The cephalorachidian liquid pressure control device comprises a body which can be cylindrical or any other geometrical shape, made from a biocompatible and stable rigid plastic or other material having similar features. The lower part of the body has one or several holes and the upper part has and internal threaded portion. It also comprises a threaded cap made from a biocompatible and stable rigid plastic or other material having similar features and having at the center thereof a hole in which is mounted a bellows shaped elastic element controlling the drain pressure. This bellows shaped elastic element has one or more ripples or any other shape allowing to act as a spring, and being provided in one of its ends with a disk shape, being part of the flow block mechanism (check). However, this flat and circular shape is not necessarily integrated to the elastic element acting as a spring.

The pressure control bellows, made from a biocompatible and stable elastic material, blocks or allows the passage of fluids by bearing with variable pressure or withdrawing from the lower base of the device's body. In this way, the opening and closing pressure is controlled within a preset range of pressure and accompanying liquid flow in the time unit. The setting variation is achieved by oppressing the pressure control bellows against the hole by rotation of the threaded valve.

OBJECTS OF THE INVENTION

The main purpose of the invention is to provide a device that being integrated to the valve, controls the pressure drain range of the cephalorachidian liquid located in the brain's ventricles, and which can be assembled in any place of the cephalorachidian liquid bypass system configuration from the brain's ventricles to the right auricle (atrium dextrum) or the peritoneal cavity.

The arrangement of the three elements comprising the device results in a drain control equipment that keeps the normal pressure in the brain's ventricles. The flow (F) passing through the equipment is set by the difference in pressure (dP) in one and other points of the system and the resistance (R) thereof, given by the pressure control device, wherein $F=dP/R$. The resistance of the equipment is mainly determined by the device integrated to the pressure control valve, which is set to open or close within the specifically preset pressure range. With higher pressures, the resistance (R) of the valve is surpassed and drains to level the pressures of the catheters of the system.

The present invention achieved very regular pressure-flow curves in the different tests of a control valve or under comparative studies between different equipment from our production, and against other equipment from other brands, changing the flow range between one test and another. The pressure remaining in the ventricles in physiological terms with a high confidence level, which is reflected in the well-being and security of the patient.

By the above characteristics the present invention constitutes a novelty having the peculiarity of improving in a notable way the operation of the cephalorachidian liquid bypass systems used in the hydrocephalus treatment due to it's hydrodynamic control features. In each unit is set the flow opening and closing function, with the purpose to adapt each equipment to the drain requirements of such liquid for each patient, which allows ensuring the good evolution thereof. Further, the manufacture of such device is simple and economical.

DETAILED DESCRIPTION OF THE INVENTION

Figure 1:
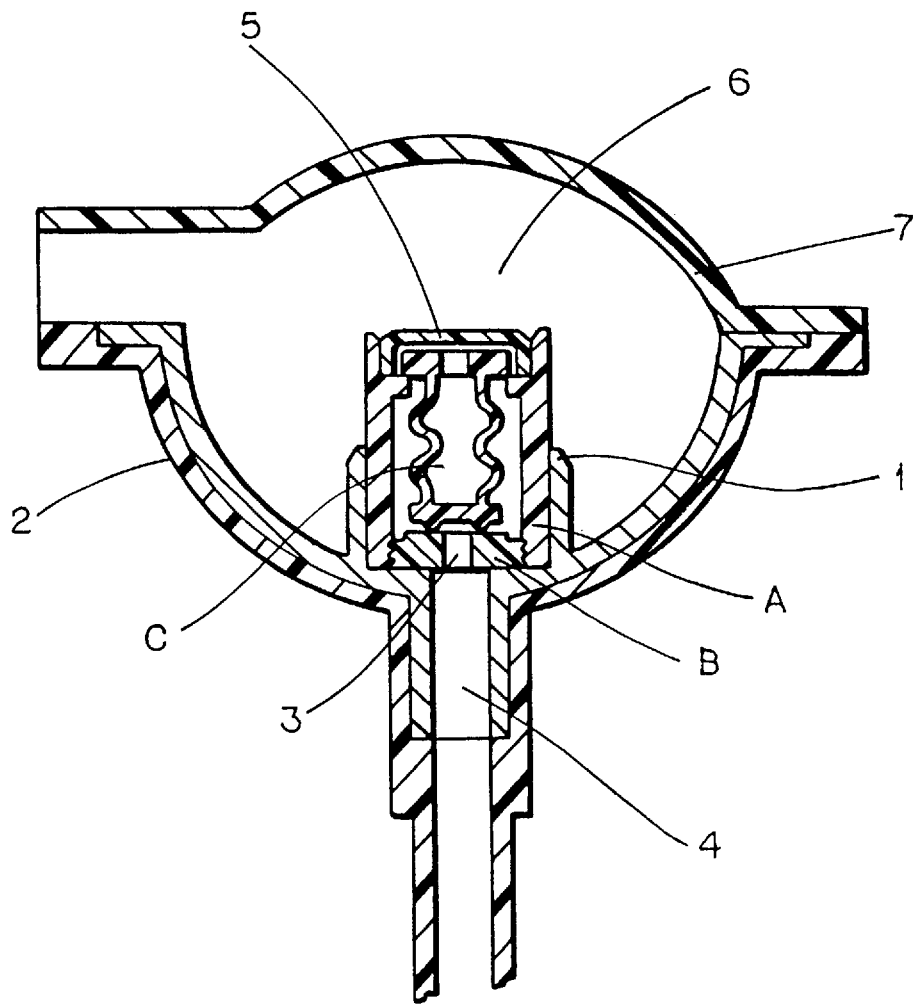
FIG. 1 is a sectional view of the pressure control device shown in a flow block position.

The invention refers to a cephalorachidian liquid pressure control device. (FIGS. 1 and 2) that can be assembled in any place of the cephalorachidian liquid bypass system and from the brain's ventricles to the right auricle or the peritoneal cavity, and having the virtue of keeping the normal pressure in the brain's ventricles or the preset ideal pressure for each patient, according to the surgeon's criteria.

The assembly of the pressure control device, by example, in a conventional type single cavity system (FIG. 3), is made in the central part of the core, located in the lower dome 2. The pressure control device has an entrance hole 3, coinciding with the opening of a entrance tube of the brain's catheter. The f low exits the device by an exit perforation 5 towards the cavity 6 formed by the assembly of the upper dome 7 with the lower dome 2.

Figure 2:
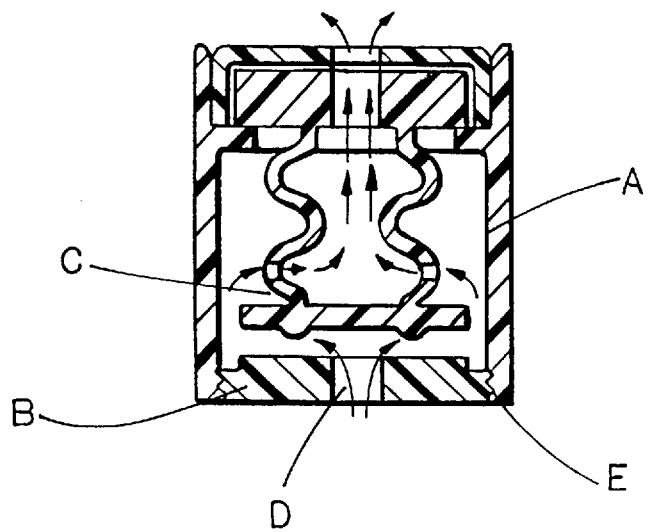
FIG. 2 is also a sectional view of said device shown in position allowing the cephalorachidian liquid flow therethrough.
Figure 5:
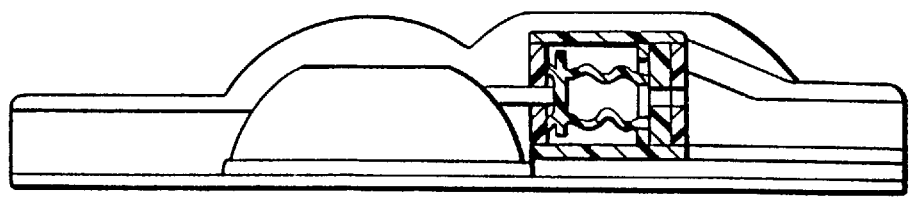
FIG. 5 is a sectional view or the prior figure system.
Figure 4:
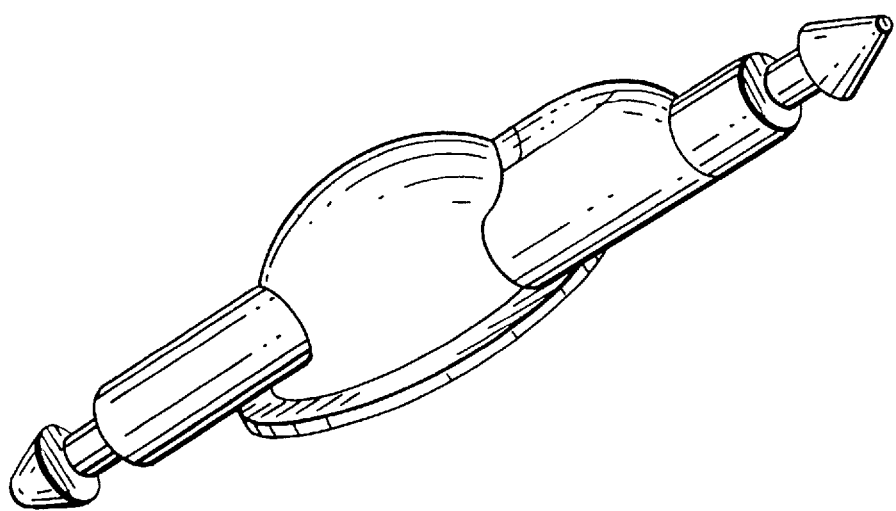
FIG. 4 is a view of a flat base system including the control device of this invention.
Figure 7:
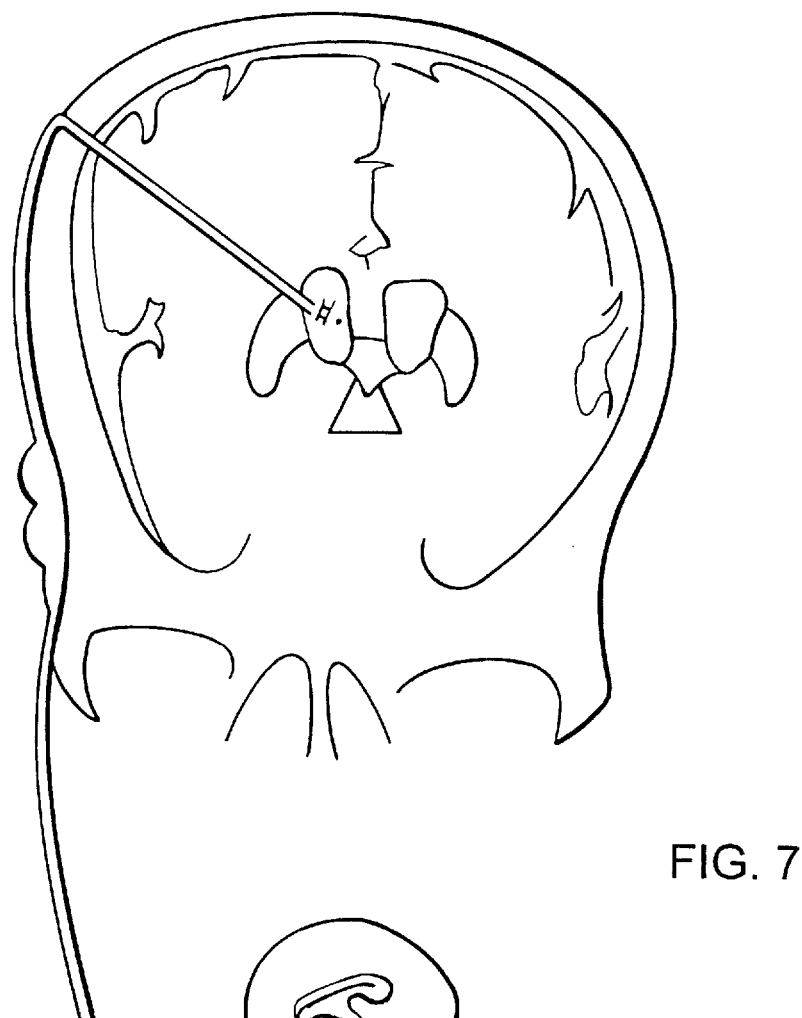
FIG. 7 is a schematical view of the head of a patient shown in the prior figure.
Figure 6:
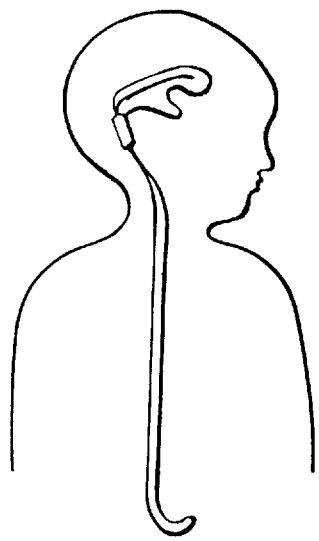
FIG. 6 is a schematical view of a patient provided with the system incorporating the device of this invention.

Referring to FIGS. 1 and 2, the pressure control device comprises parts A, B and C. The latter interacts with the base of part A and it is there where pressure Is controlled. Part A is made with a biocompatible and stable rigid plastic or other material having similar consistency and it can be cylindrical or any other geometric shape. Lower part of part A has one or several perforations (see D in FIG. 2) and the upper part has a internally threaded section (E).

Part (B) is a threaded cap made from a biocompatible and stable rigid plastic or other material having similar consistency, having at its center a perforation (P) in which the bellows or pressure control elastic element (C) is mounted. The circular movement of the cap allows the setting of the equipment.

Figure 3:
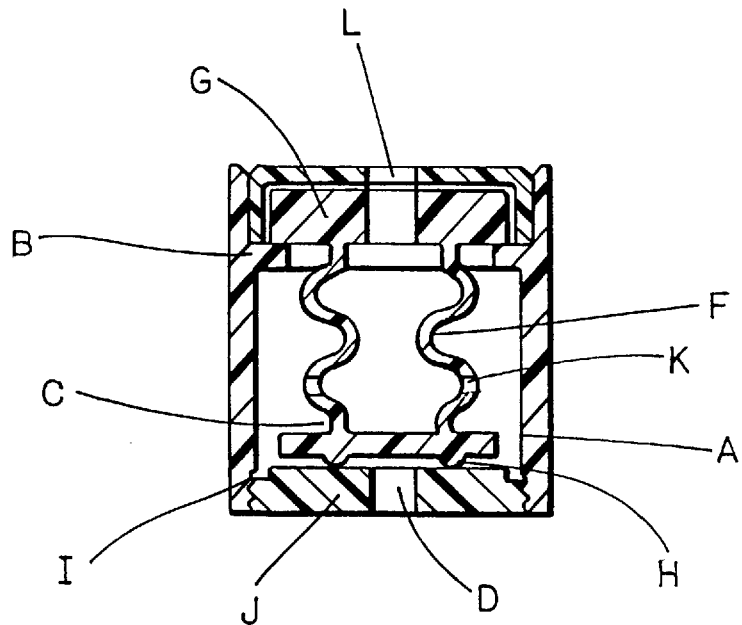
FIG. 3 illustrates the device of the present invention incorporated in a conventional type, single cavity bypass system.

Part (C) or the pressure control bellows is a elastic element having such shape with one or several ripples or any other shape allowing it to act as a spring and made from an elastomeric biocompatible and material. In one of its ends (G) is held to part (B) and in the other has a disk or any other shape (H) having in its free face a annular rim or any other surface finish (I). It forms part of the flow block mechanism (check). By bearing on the internal flat base (J) of part (A), it hermetically blocks the one or several perforations (D) and stops the flow when the entrance fluid pressure is lower than the mechanical pressure applying part (C). It also blocks fluid return, making unidirectional flow. However, not necessarily such circular plate (H) being integrated to the elastic element acting as a spring. This part (C) has one or several perforations (K) allowing the passage of the cephalorachidian liquid into part (C) and exists by the hole (L) of part (c) towards the distal drain tube (FIG. 3).

It is to be noted that the best method to carry out the practice of the invention cited, is that inferred from the prior specification.

I claim:

1. An intraventricular pressure control device for draining the cephalorachidian liquid in the hydrocephalus comprising a cylindrical body having a lower base with one or more perforations and an upper part comprising an internally threaded section and a threaded cap having a central perforation; said cap is threadedly coupled to said upper part of the cylindrical body; and pressure control bellows positioned inside the body to act as an element which allows or prevents the circulation of cephalorachidian liquid through the device; said bellows comprising:

a) an upper section being fixed between the cap and a rim in the internal wall of the body, and including a perforation which is in register with the perforation of the cap;

b) an elastic middle section having perforations, and which is unitary to the upper section, forming a lower passage to allow the flow of cephalorachidian liquid towards distal parts of the system for draining such liquid; said middle section is able to contract and expand in response to a predetermined liquid pressure; thus controlling the opening and closing pressure in a predetermined range of pressure and liquid flow per time unit; and c) a lower section having a blocking element supported on the lower base of the cylindrical body, which allows or prevents the pass of liquid through the device.

2. The device of claim 1, wherein the blocking element comprises a disk shape part, having on its lower face an annular rim, that upon making contact with the base of the body, hermetically obstructs the one or several perforation thereof and thereby stopping the flow of fluid when the entrance pressure of the fluid is lower than the mechanical pressure exerted by the elastic element.

3. The device of claim 1, wherein the blocking element prevents the return of the fluid, thus the flow is unidirectional.

4. The device of claim 2, wherein the disk part forms part of the elastic section.

5. The device of claim 2, wherein the disk part does not form part of the elastic section.

6. The device of claim 1, wherein the adjustment of the pressure is achieved in the device by adjusting the pressure of the bellows against the base of the body, by rotating the threaded cap.

7. The device of claim 1, wherein the bellows is an elastic element functioning as a spring.

8. The device of claim 1, wherein the bellows has one or more ripples.

9. The device of claim 1, wherein the elements are made from a biocompatible and stable material.

10. An intraventricular pressure control device for draining the cephalorachidian liquid in the hydrocephalus comprising a cylindrical body having a lower base with one or more perforations and an upper part comprising an internally threaded section and a threaded cap having a central perforation; said cap is threadedly coupled to said upper part of the cylindrical body; and pressure control bellows positioned inside the body to act as an element which allows or prevents the circulation of cephalorachidian liquid through the device; said bellows comprising:

a) an upper section being fixed between the cap and a rim in the internal wall of the body, and including a perforation which is in register with the perforation of the cap;

b) an elastic middle section having perforations, and which is unitary to the upper section, forming a lower passage to allow the flow of cephalorachidian liquid towards distal parts of the system for draining such liquid; said middle section is able to contract and expand in response to a predetermined liquid pressure; thus controlling the opening and closing pressure in a predetermined range of pressure and liquid flow per time unit; and c) a lower section having a blocking element supported on the lower base of the cylindrical body, which allows or prevents the pass of liquid through the device;

wherein said device can be connected to a cephalorachidian liquid bypass system from the brain's ventricles to the right auricle or peritoneal cavity.

* * * * *